United States Patent [19]

Jones et al.

[11] 4,320,112
[45] Mar. 16, 1982

[54] COMPOSITION FOR PEST REPELLENT RECEPTACLE

[76] Inventors: Lonnie R. Jones, P.O. Box 188; Joseph L. Hill, P.O. Box 3784, both of Wilson, N.C. 27893

[21] Appl. No.: 157,063

[22] Filed: Jun. 6, 1980

[51] Int. Cl.³ .................... A01N 25/34; A01N 35/00; A01N 27/00
[52] U.S. Cl. ........................................ 424/19; 424/27; 424/29; 424/30; 424/78; 424/333; 424/356; 424/DIG. 10
[58] Field of Search .................. 424/78, 19, 27, 29, 424/30, 333, 356, DIG. 10

[56] References Cited
U.S. PATENT DOCUMENTS

| 397,259 | 2/1889 | Tsheppe | 424/29 |
| 1,512,104 | 10/1924 | Kennedy | 424/29 |
| 2,587,957 | 3/1952 | Bauer et al. | 424/29 |
| 3,132,992 | 5/1964 | Kimmel | 424/30 |
| 3,567,119 | 10/1969 | Wilbert et al. | 424/29 |
| 3,590,118 | 6/1971 | Conrady et al. | 424/29 |
| 3,694,543 | 9/1972 | Needham et al. | 424/30 |
| 3,767,785 | 10/1973 | Bordenca | 424/29 |
| 3,857,934 | 12/1974 | Berstein et al. | 424/30 |
| 3,864,468 | 2/1975 | Hyman et al. | 424/29 |
| 4,097,607 | 6/1978 | Larson | 424/333 |
| 4,164,561 | 8/1979 | Hautmann | 424/DIG. 10 |
| 4,193,986 | 3/1980 | Cox | 424/28 |

FOREIGN PATENT DOCUMENTS 2618975 11/1977 Fed. Rep. of Germany ......424/DIG. 10

OTHER PUBLICATIONS

The Merck Index, 9th ed., (1976)–items 6194 and 2310.

Primary Examiner—Douglas W. Robinson

[57] ABSTRACT

A receptacle such as a plastic trash can or bag contains an insect and animal repellent for ridding areas containing the receptacles of annoying insects and for preventing animals from turning over or destroying the receptacles when full, avoiding unnecessary clean-ups and possible health hazards. Preferably, the pest repellent is incorporated into the receptacle during the forming thereof. Effective amounts of naphthalene flakes and oil of citronella added in solid form to the synthetic resin forming the receptacle provides for the insect and animal repellent properties.

4 Claims, No Drawings

COMPOSITION FOR PEST REPELLENT RECEPTACLE

BACKGROUND OF THE INVENTION

Field of the Invention

This invention relates to an insect and animal repellent receptacle, and more particularly to a plastic trash receptacle having incorporated therein an active pest repellent additive to ward off annoying insects and prevent animals for toppling and opening the filled trash receptacles.

Disclosure Statement

Pest repellent articles are well-known, moth balls being a typical example of such an article. Likewise, containers formed from extruded synthetic resin sheets in which an insect repellent compound has been added is disclosed in U.S. Pat. No. 3,767,785, issued Oct. 23, 1973, to Bordenca, the patent disclosing adding a specific organic insect repellent compound to formed sheet material to provide the desired results. An animal deterrent composition comprising cinnamic aldehyde which can be applied as a coating to various objects, such as an animal stall, bandage or cast on the animal or a collar on the animal for deterring the animal from chewing or otherwise damaging the objects is disclosed in U.S. Pat. No. 4,097,607, issued June 27, 1978, to Larson, U.S. Pat. Nos. 3,857,934, issued Dec. 31, 1974, to Bernstein et al, and 3,864,468, issued Feb. 4, 1975, to Hyman et al. disclose non-porous, polymeric articles having active properties, such as antibacterial, antifungal, pesticidal, insecticidal, animal repellent, etc., in which the surface of the articles is coated with the active agent, the active agent migrates or moves throughout the body of the article to which it is applied to impart an effective level of activity throughout the article and/or on a surface other than the one to which the active agent has been applied. Mosquito and insect repellants in general have been typically applied to the skin to prevent mosquito and insect bites. U.S. Pat. No. 3,590,118, issued June 29, 1971, to Conrady et al., discloses a variety of such mosquito repellent compositions in which the repellents are dissolved in interpolymer resins of alpha-beta olefinically unsaturated carbonyl monomers. The solutions are found to be slow release systems for the repellent compounds when spread and dried as films on substrates, such as the skin of humans and animals. One such known mosquito repellent disclosed by the patent is oil of citronella, a compound which has long been used to repel mosquitoes.

The pest repellent receptacle of the present invention is provided with both insect and animal repellent properties, such that when used as a trash receptacle annoying insects, such as flies, and animals which can topple or rip open such plastic trash receptacles are repelled by the odor, leaving the trash receptacle and area therearound substantially free of all pests. Preferably, the pest repellent properties are provided by an active ingredient comprising a mixture of citronella oil and naphthalene flakes which are compounded with the synthetic resin forming the trash receptacle. As mentioned above, citronella oil is a well-known insect repellent. Naphthalene is also known for moth repellent properties. However, a mixture of the two components in accordance with the present invention repels both insects and animals, such as household pets, preventing the animals from turning over or ripping open the trash receptacle, thus annoying clean-up operations and hazardous and unhealthy environments are avoided.

SUMMARY OF THE INVENTION

In accordance with the present invention, there is provided a pest repellent receptacle, more particularly a trash receptacle formed of synthetic resin which has contained therein a composition which has insect and animal repellent properties. The pest repellent properties are provided by an active ingredient which is incorporated into the synthetic resin and comprises a mixture of citronella oil and naphthalene flakes. The active mixture is preferably incorporated into the synthetic resin prior to extrusion or molding to form the receptacle by mixing the pest repellent active agent mixture with the plastic pellets and then forming the articles. The amount of active ingredient mixture added to the synthetic resin depends upon the use of the receptacle and the thickness of the article which is to be produced. Enough of the active ingredient is added to produce the intended result, while avoiding an undue excess of the active agent, which is costly and can produce an excessive odor.

The pest repellent receptacle of the present invention exhibits repellent properties toward a wide spectrum of insects, such as, for example, moths, mosquitoes, ants, beetles, house flies, and the like, and is also capable of repelling animals, such as common household pets, including cats and dogs.

Accordingly, it is an object of the present invention to provide a pest repellent receptacle for repelling insects and other animals from the receptacle environment.

Another object of the present invention is to provide a container which can maintain an insect-free and animal-free environment in cases where a variety of food and products are stored, transported, or dispensed in the container.

Another object of the present invention is to provide a plastic receptacle having incorporated therein a pest repellent composition for repelling pests such as insects and other animals.

Still another object of the invention is to provide a novel pest repellent composition which can be incorporated into articles and which is capable of repelling insects and other animals.

These together with other objects and advantages which will become subsequently apparent reside in the features of the pest repellent receptacle and the pest repellent active ingredient as more fully hereinafter described and claimed.

DETAILED DESCRIPTION OF THE INVENTION

The pest repellent active ingredient of the present invention may be applied to any article, such as those articles disclosed in U.S. Pat. No. 3,762,785, but has particular utility in the forming of pest repellent receptacles to maintain an insect-free environment in cases where a variety of food and other products susceptible to insect infestation are stored, transported or dispensed in such receptacles. Likewise, the active ingredient, added to a receptacle for storing or disposing of trash, deters animals, such as common household pets, from disturbing the receptacles, which typically have been over-turned or ripped open by such pets, necessitating the annoying task of cleaning up the spilled contents.

The receptacles can be constructed into a variety of forms, e.g., drums, barrels, boxes, bags, etc., of varying sizes and thickness depending upon the function of the receptacle being produced.

The active ingredient can be added to all types of construction materials, such as those disclosed in mentioned U.S. Pat. No. 3,767,785, but receptacles formed of plastic materials are preferred. Synthetic polymers which can be used to form the receptacles include cellulose acetate, polyethylene, polypropylene, polystyrene, etc., or co-polymers of the respective monomers. The synthetic resin is molded or extruded in the form of the receptacle or formed into a plurality of sheets which are then laminated to form the desired receptacle shape. The invention has particular utility in providing insect-proof and animal deterrent properties to plastic trash bags, typically used in households as liners for trash barrels or cans or as a trash disposal means. Such trash bags usually are made of extruded polyethylene which is formed into sheets of varying thicknesses, depending upon the use of the trash bag. The polyethylene sheets are then laminated to form the receptacle. Such trash bags are also produced by blow molding to form the entire receptacle.

The active ingredient which provides both the insect and animal repellent properties of the receptacles comprises a mixture of naphthalene flakes and oil of citronella, both of which are known as insect or moth repellent compositions, but have not been previously mixed together.

The pest repellent receptacles formed in accordance with the present invention may be formed by incorporating the active ingredient on the surface of the receptacle in a variety of ways. The method of incorporation will depend, in part, upon the particular type of receptacle which it is desired to employ. For example, the active ingredient may be incorporated on the surface of the receptacle by immersing the receptacle in a solution containing the active ingredient, or the active ingredient may be incorporated on the surface by applying a solution of the active ingredient by coating the web, such as by brushing, rolling, spraying, or any other type of common coating application technique. While applying the active ingredient to the surface of the receptacle provides adequate results, surface coatings tend to wear off, in particular, when the receptacles, such as trash bags are packaged or stored one on top of the other, friction between the receptacles tending to wear off the surface coating. Even storage at long lengths of time will tend to reduce the effect of the active ingredient, unless the coating is of such thickness so as to produce an undesirable odor. Such surface coatings can also be somewhat toxic to small children and small pets if applied in excessive amounts.

Preferably, the active ingredient of this invention is incorporated in or on the polymers and co-polymers which form the receptacles prior to extrusion or molding by mixing the active ingredient with the plastic pellets and extruding or molding the mixture into the formed receptacle. The naphthalene and oil of citronella are preferably added to the dry plastic powder in dry form, although any form of the active ingredient which will blend well with the synthetic resin forming the receptacle can be utilized.

The amount of the active ingredient which can be incorporated in the pest repellent receptacle can vary depending upon the uses and thickness of the receptacle. Receptacles formed into heavy-duty trash barrels will require slightly more amounts of the active ingredient than would the plastic trash bag, now commonly used in households. Depending upon the use and thickness of the receptacle, the active ingredient mixture is added in amounts ranging from about 5% to 25% of the total weight of the receptacle. Slightly smaller or larger amounts of the active ingredient can also be effective depending upon the desired use of the pest repellent receptacle. The amount of naphthalene added to the synthetic resin forming the receptacle can vary between about 4% to 20% by weight. The oil of citronella can vary between about 1% to 5% by weight of the pest repellent receptacle. The ratio of naphthalene flakes to oil of citronella added can range from about 4:1 to 16:1.

The following example is intended to illustrate the invention but not to limit the scope thereof, parts and percentages being by weight unless otherwise specified:

EXAMPLE

A pest repellent container was formed by mixing in dry form;
87% polyethylene resin,
12% naphthalene flakes and
1% citronella oil.

The mixture was thoroughly blended and a plastic container was formed by blow molding the blended mixture. The container was less than ⅛" thick.

The container was tested for its animal repellent properties by placing the container in an environment frequented by a household pet. Once placed, the container deterred the animal from stopping at the location. Furthermore, since the active ingredient included known insect repellent compounds, no insect infestation was expected.

The present invention enables receptacles, particularly those receptacles utilized to store and dispose of refuse to maintain an insect-free and animal-free environment, eliminating annoying insect infested areas and clean-up operations and enables the maintenance of a healthful environment. Receptacles containing the pest repellent active ingredient of the present invention can be formed into a variety of trash receptacles commonly used in households, such as thin-walled plastic trash bags, thick-walled plastic trash bags, such as for heavy-duty use, larger plastic garbage cans, etc. The receptacles can also be in other forms including moth repellent storage bags for clothes or other cloth goods.

The foregoing is considered as illustrative only of the principles of the invention. Further, since numerous modifications and changes will readily occur to those skilled in the art, it is not desired to limit the invention to the exact construction and composition described, and accordingly, all suitable modifications and equivalents may be resorted to, falling within the scope of the invention.

What is claimed as new is as follows:

1. A pest repellent receptacle useful for holding trash and formed from a synthetic resin, said resin having about 5 to 25% by weight of an active ingredient mixed therein prior to the formation of the receptacle, said active ingredient comprising naphthalene and citronella oil in amounts capable of repelling insects and other animals, the ratio of naphthalene to citronella oil being in the range from about 4:1 to about 16:1 by weight.

2. The receptacle of claim 1 wherein said receptacle is in the form of a plastic trash bag.

3. The receptacle of claim 1 wherein said naphthalene is added in amounts of about 4% to 20% by weight and said citronella oil is added in about 1% to 5% by weight of said synthetic resin.

4. The receptacle of claim 3 wherein said synthetic resin is polyethylene.

* * * * *